United States Patent
Prabhune et al.

(10) Patent No.: US 10,709,743 B2
(45) Date of Patent: Jul. 14, 2020

(54) PHARMACEUTICAL WOUND HEALING COMPOSITION

(71) Applicant: Council of Scientific and Industrial Research, New Delhi (IN)

(72) Inventors: Asmita Ashutosh Prabhune, Maharashtra (IN); Snehal Vijay More, Maharashtra (IN); Sachin Bharat Agawane, Maharashtra (IN)

(73) Assignee: Council of Scientific & Industrial Research, New Delhi (IN)

( * ) Notice: Subject to any disclaimer, the term of this patent is extended or adjusted under 35 U.S.C. 154(b) by 57 days.

(21) Appl. No.: 15/760,993

(22) PCT Filed: Sep. 20, 2016

(86) PCT No.: PCT/IN2016/050315
§ 371 (c)(1),
(2) Date: Mar. 16, 2018

(87) PCT Pub. No.: WO2017/051433
PCT Pub. Date: Mar. 30, 2017

(65) Prior Publication Data
US 2018/0264051 A1    Sep. 20, 2018

(30) Foreign Application Priority Data
Sep. 22, 2015 (IN) .......................... 2996/DEL/2015

(51) Int. Cl.
| | |
|---|---|
| *A61K 35/62* | (2006.01) |
| *A61L 26/00* | (2006.01) |
| *A61P 17/02* | (2006.01) |
| *A61K 9/00* | (2006.01) |
| *A61K 9/06* | (2006.01) |
| *A61K 47/38* | (2006.01) |
| *A61K 36/064* | (2006.01) |

(52) U.S. Cl.
CPC ............ *A61K 35/62* (2013.01); *A61K 9/0014* (2013.01); *A61K 9/06* (2013.01); *A61K 47/38* (2013.01); *A61L 26/0047* (2013.01); *A61L 26/0066* (2013.01); *A61L 26/0076* (2013.01); *A61P 17/02* (2018.01); *A61K 36/064* (2013.01); *A61K 2236/11* (2013.01); *A61K 2300/00* (2013.01)

(58) Field of Classification Search
None
See application file for complete search history.

(56) References Cited

U.S. PATENT DOCUMENTS

| | | |
|---|---|---|
| 5,981,497 A | 11/1999 | Maingault |
| 2015/0094273 A1 | 4/2015 | Prabhune et al. |

FOREIGN PATENT DOCUMENTS

| | | |
|---|---|---|
| CN | 103990175 A | 8/2014 |
| WO | WO-2013/112875 A1 | 8/2013 |
| WO | WO-2015/170342 A1 | 11/2015 |

OTHER PUBLICATIONS

Aramwit et al., "The Effects of Sericin Cream on Wound Healing in Rats", Biosci. Biotechnol. Biochem., vol. 71, No. 10, 2007, pp. 2473-2477.
M. N. Padamwar et al., "Silk Sericin and Its Applications: A Review", Journal of Scientific & Industrial Research, vol. 63, Apr. 2004, pp. 323-329.
International Search Report and Written Opinion for PCT/IN2016/050315, dated Mar. 10, 2017, 11 pages.
Aramwit, et al., "Silk Sericin Ameliorates Wound Healing and Its Clinical Efficacy in Burn Wounds", Archives of Dermatological Research, 2013, 305(7), pp. 585-594.
Fan et al., "Antioxidant Activities of Silk Sericin from Silkworm *Bombyx mori*", Journal of Food Biochemistry, 2009, 33(1), pp. 74-88.
Teramoto H et al., "Preparation of Gel Gilm from Bombyx Mori Silk Sericin and Its Characterization as a Wound Dressing", Bioscience, Biotechnology, and Biochemistry, Dec. 2008; 72(12); pp. 3189-3196.
Padamwar MN et al., "Silk Sericin as a Moisturizer: An in Vivo Study", Journal of Cosmetic Dermatology, 2005, 4(4), pp. 250-257.

*Primary Examiner* — Susan Hoffman
(74) *Attorney, Agent, or Firm* — Blank Rome LLP

(57) ABSTRACT

The present invention discloses a biodegradable and biocompatible pharmaceutical composition comprising silk Sericin, sophorolipid, a gelling or thickening agent and one or more pharmaceutically acceptable carriers or excipients for faster wound healing and limit scarring.

6 Claims, 5 Drawing Sheets

PHARMACEUTICAL WOUND HEALING COMPOSITION

RELATED APPLICATIONS

This application is a national phase of PCT/IN2016/050315, filed on Sep. 20, 2016, which claims the benefit of Indian Application No. 2996/DEL/2015, filed on Sep. 22, 2015. The entire contents of those applications are hereby incorporated by reference.

FIELD OF THE INVENTION

The present invention relates to biodegradable and biocompatible pharmaceutical composition for wound healing. More particularly, the invention relates to composition comprising silk sericin and sophorolipid for the management of faster wound healing and limits scarring.

BACKGROUND AND PRIOR ART

Wound healing is a complicated process in which the skin repairs itself after injury. The normal wound healing process can be broadly classified into three stages namely the inflammatory, proliferative and maturation phases. The inflammatory phase that lasts up to two days involves an orderly recruitment of cells to the wound area, which is followed by proliferative phase lasting up to 6 days. In this phase, the fibroblasts, keratinocytes and other cells in the wound bed begin to actively proliferate to close the wound. The maturation phase follows the proliferative phase, will take about two weeks, by which time the wound will be completely healed by restructuring the initial scar tissue.

However, certain wounds are problematic and do not follow the normal time table for the healing process, will take longer time to heal. Thus the problematic wounds associated with additional attention, pain management and with increased costs.

Re-epithelialization is a critical step in wound healing; in which epidermal keratinocytes laterally migrate to close a wound. However, in chronic wounds, keratinocyte migration is blocked and the wounds remain open, causing more harm to the patients.

Oxygen has a significant role in wound healing, being essential to provide the additional energy source for the repairing process. It has been shown in numerous clinical studies that in typical wound, partial pressures of oxygen are markedly reduced and may be the rate limiting process in wound repair. Also, supplemental oxygen has been shown to enhance healing dependent on dose and frequency. Therefore, the availability of oxygen may, in fact, be one of the rate limiting steps in early wound repair.

Further, most wounds heal rapidly and efficiently but the results are not perfect, as the healing process leaves scar on the skin. Scar tissue is less flexible than normal skin and can be cosmetically disfiguring affected area.
As is evident from the above, the two major goals of wound healing (tissue repair) which includes rapid healing and complete reconstruction of the damaged area without leaving scar.

Apart from the synthetic would healing compositions, also, there is literature available on biocompatible compositions in the prior art for wound healing and methods of use thereof.

US20150094273 discloses synergistic pharmaceutical composition comprising an antibiotic and sophorolipid, to effectively combat the problem of antibiotic resistance by increasing the permeability of the antibiotic drugs across the outer membrane of bacteria. The sophorolipid being amphiphilic in nature can span through the structurally alike cell membrane and facilitate the entry of antibiotic drug molecules.

Article titled "*Silk sericin ameliorates wound healing and its clinical efficacy in burn wounds*" by Pornanong Aramwit et al. published in *Archives of Dermatological Research*, 2013, 305(7), pp 585-594 reports evaluate the effect of silk sericin, a protein from silkworm cocoon, on scratch wound healing in vitro. For applicable result in clinical use, author also study the efficacy of sericin added to a standard antimicrobial cream, silver zinc sulfadiazine, for open wound care in the treatment of second-degree burn wounds.

Project title "*Purified rhamnolipids/sophorolipids biomedical applications including cutaneous wound healing*" by Prof. Ibrahim Banat, Prof. Christopher Mitchell, Prof. Roger Marchant reports biomedical applications of rhamnolipids/sophorolipids including cutaneous wound healing.

Article titled "*Silk sericin and its applications: A review*" by M N Padamwar et al. published in *Journal of Scientific & Industrial Research*, 2004, 63, pp. 323-329 reports silk consists of two types of proteins, silk fibroin and sericin. Sericin contributes about 20-30 percent of total cocoon weight. It is characterized by its high content of serine and 18 amino acids, including essential amino acids. There are different methods of isolation of sericin from silk thread. Solubility, molecular weight, and gelling properties of sericin depend on the method of isolation. It has wide applications in pharmaceuticals and cosmetics such as, wound healing, bioadhesive moisturizing, antiwrinkle and antiaging.

U.S. Pat. No. 5,981,497 discloses utilization of sophorolipids as therapeutically active substances or cosmetic products, in particular for the treatment of the skin. This invention relates to a new use of a sophorolipidic compound, of pharmaceutically acceptable salts of the acidic form of the sophorolipid, and of the ester of the deacetylated sophorolipidic acid form as therapeutically active substances in a method for therapeutic treatment of the human or animal body, and more particularly as an activator of macrophages, as a fibrinolytic agent, as a healing agent, as a desquamating agent, and as a depigmenting agent.

Article titled "*Antioxidant activities of silk sericin from silkworm Bombyx Mori*" by Jin-Bo Fan et al. published in *Journal of Food Biochemistry*, 2009, 33(1), pp 74-88 reports investigation of the free-radical-scavenging activity and antioxidant activity of silk sericin. Silk sericin was prepared from silkworm *Bombyx mori* and its ability to scavenge hydroxyl, superoxide and 1,1-diphenyl-2-picrylhydrazyl (DPPH) radicals was determined by Electron Spin Resonance (ESR) and ultraviolet spectrophotometry, respectively. The antioxidant activities of the silk sericin, including lipid peroxidation in the linoleic acid system, reducing power and ferrous-ion-chelating ability, were evaluated. The results showed that silk sericin had a strong scavenging capacity for hydroxyl, superoxide and DPPH radicals. The results also showed that silk sericin had potent antioxidative activity on the peroxidation of linoleic acid. The reducing power and ferrous-ion-chelating ability of silk sericin were significant. These results indicated that silk sericin from silkworm *B. mori* was a natural antioxidant with potent antioxidative activity.

Article titled "*The effects of sericin cream on wound healing in rats*" by Aramwit P. et al. published in *Bioscience, Biotechnology, and Biochemistry*, 2007, 71(10):2473-7 reports sericin has good hydrophilic properties, compatibility, and biodegradation, it can be used as a wound-healing agent. Author evaluated the effects of sericin on wound healing and wound size reduction using rats by generating two full-thickness skin wounds on the dorsum. Group 1 animals were treated with Betadine on left-side (control) wounds and, with 8% sericin cream on right-side (treated) wounds. Group 2, cream base (formula control) and 8% sericin cream (treated) were topically applied to left-, and right-side wounds respectively. Sericin-treated wounds had much smaller inflammatory reactions, and wound-size reduction was much greater than in the control throughout the inspection period. Mean time in days for 90% healing from sericin-treated wounds was also much less than for cream base-treated wounds. Histological examination after 15 d of treatment with 8% sericin cream revealed complete healing, no ulceration, and an increase in collagen as compared to cream base-treated wounds, which showed some ulceration and acute inflammatory exudative materials.

Article titled "*Preparation of gel film from Bombyx mori silk sericin and its characterization as a wound dressing*" by Teramoto H et al. published in *Bioscience, Biotechnology, and Biochemistry,* 2008 December; 72(12):3189-96 reports sericin is a highly hydrophilic protein family acting as the glue in *Bombyx mori* silk. In order to apply sericin as a wound dressing, a novel sericin film named gel film was prepared by a simple process without using any chemical modifications: sericin solution was gelled with ethanol into a sheet shape and then dried. Infrared analysis revealed that the sericin gel film contained water-stable beta-sheet networks formed in the gelation step.

CN103990175 discloses a pharmaceutical controlled release bilayer nano-fiber wound dressing and preparation method. A two-layer wound dressing nanofibers controlled drug release function, wherein: the water-soluble natural polymer is sericin, hyaluronic acid, sodium alginate, water-soluble chitosan, in order to improve the water-soluble natural polymer can be spun to introduce co-spun polymer polyvinyl alcohol (PVA), polyvinylpyrrolidone (PVP), polylactic acid (PLA), in which the natural polymer and co-polymer spinning the mass ratio of 4:1~1:10.

PCT Application WO2013112875A1 discloses Wound dressings with enhanced gas permeation and other beneficial properties. A first embodiment of this invention provides a wound dressing comprising a wound dressing substrate including gas vesicles, rhamnolipids, and sophorolipids. A second embodiment provides a wound dressing as in the first embodiment, wherein the wound dressing substrate includes a wound dressing hydrogel. A third embodiment provides a wound dressing as in either the first embodiment or the second embodiment, wherein the wound dressing hydrogel comprises a polymer selected from the group consisting of polyvinyl alcohol, alginate, chitosan, carboxyethyl chitosan, methylcellulose, gelatin, soy protein, wheat protein, xanthan gum, gum arabic, polyacrylamide, polyalcohols, polysaccharides, polyamines, proteins, or mixtures thereof. Article titled "*Silk sericin as a moisturizer: an in vivo study*" By Padamwar M N et al. published in *Journal of Cosmetic Dermatology,* 2005, 4(4), pp 250-257 reports Sericin gels were prepared using sericin solution and with pluronic and carbopol as stabilizers. The gels were applied on the skin of healthy human volunteers and its moisturizing efficiency was evaluated by measuring the skin hydroxyproline content, impedance, TEWL, and scanning electron microscopy (SEM) results.

In the light of the foregoing, it is evident that although many methods have been proposed and tested to promote wound healing and limit scarring; however, cost-effective methods and compositions are still desired to address the above out-standing issues.

OBJECTIVE OF THE INVENTION

The main objective of the present invention is to provide biodegradable and biocompatible pharmaceutical composition for wound healing.

Another objective of the present invention is to provide biodegradable and biocompatible pharmaceutical composition that heals the wounds faster and limits scarring.

Still another objective of the present invention is to provide biodegradable and biocompatible pharmaceutical composition comprising silk Sericin, sophorolipid, a gelling or thickening agent and one or more pharmaceutically acceptable carriers or excipients for faster wound healing and limit scarring.

Yet another objective of the present invention is to provide methods of administering said pharmaceutical composition.

SUMMARY OF THE INVENTION

Accordingly, the present invention provides biodegradable and biocompatible pharmaceutical composition comprising silk Sericin and sophorolipid, for faster wound healing and limits scarring.

In an aspect, the present invention provides biodegradable and biocompatible pharmaceutical composition comprising silk Sericin, sophorolipid, a gelling or thickening agent and one or more pharmaceutically acceptable carriers or excipients for faster wound healing and limit scarring.

In another aspect, the present invention provides composition that can be formulated for topical use, such as an aqueous solution, suspension, dispersion, salve, ointment, gel, cream, lotion, spray or paste.

In yet another aspect, the said composition is formulated as topical gel.

In another aspect, the present invention provides a process for the preparation of topical gel.

In yet another aspect, the present invention provides methods of administering said pharmaceutical composition.

In further aspect, the present invention provides the method of treating wounds using said composition comprises administering an effective amount of said wound healing composition to the wounded area. The period of application will depend on the size and severity of the wound.

Figure 1:
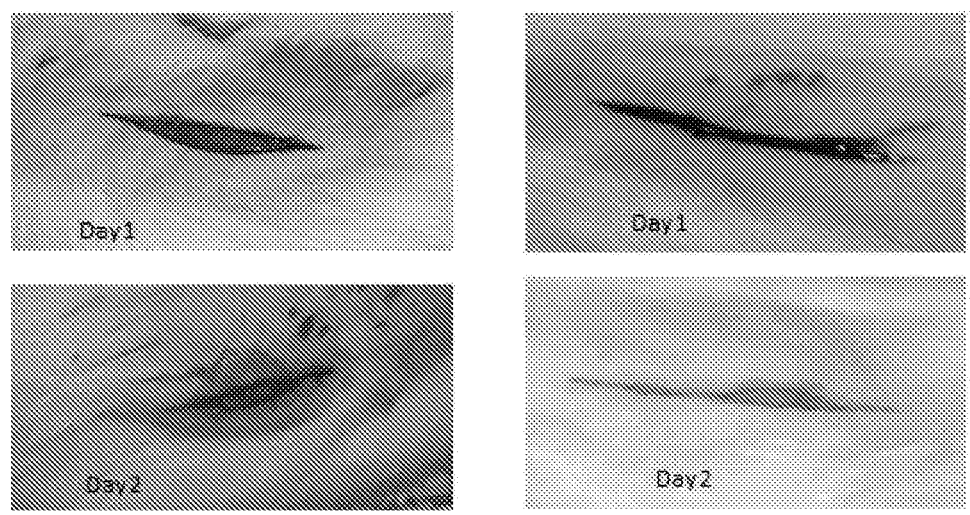
FIGS. 1 to 5 depicts the visible observation of comparative wound healing of the Wister rats by the application of control vis-à-vis group B. The group B (presented on the right side) treated with the gel according to the invention completely diminishes the scar of the wound.

Table 1 shows body weights of the animals in grams.

Table 2 depicts different test formulations.

Table 3 represents wound size measurement in rats post application of test formulations at day 2, 4, 6, 8 and 10.

DETAILED DESCRIPTION OF THE INVENTION

The invention will now be described in detail in connection with certain preferred and optional embodiments, so that various aspects thereof may be more fully understood and appreciated.

The present invention provides biodegradable and biocompatible pharmaceutical composition comprising silk Sericin, sophorolipid, a gelling or thickening agent and one or more pharmaceutically acceptable carriers or excipients for faster wound healing and limit scarring.

Sericin as used in the present composition is a protein created by Bombyx mori (silkworms) in the production of silk. Silk cocoons were purchased from Sai Techni silk Industry located in Jejuri near Pune. Use of 8 to 10% sericin is permitted by USFDA. Sericin gel is obtained by heat extraction of the cocoons of Bombyx mori. It is reported that Sericin containing food relives constipation, suppresses development of bowel cancer and accelerates the absorption of minerals. Sericin is also used in the products such as Skin, hair and nail cosmetics.

The second active, sophorolipid as used in the invention is produced using Candida bombicola (ATCC 22214) in 10% glucose solution and 1% vegetable oil by incubating the cell broth at 28° C. followed by extracting with ethyl acetate to obtain a brown colored viscous product (sophorolipid) that was stored at 4° C. One preferred vegetable oil is oleic acid. Sophorolipid produced using any other vegetable oil is also suitable for the purpose of the present invention including Linoleic, linolenic, stearic, arachidonic, arachidic and such like.

The active components viz., sericin and sophorolipids as used in the invention can be produced from renewable sources and are completely biocompatible and biodegradable. Since, the production of sophorolipid is very cost effective and the required amount in the present wound healing composition is very negligible, the invention disclosed herein is also cost-effective.

The sericin is by-product of silk industry and can be obtained easily as it is considered as waste. sericin and sophorolipid, both the components as used in the instant compositions are biocompatible and completely absorbed by the skin without any side effects. The composition according to the invention causes faster wound healing as compared to commercially available wound healing formulations. Also, the wound healing compositions leaves minimal scar in the wound area after the healing process.

The commercially available formulations cause side effects such as erythema, erosion, edematous swelling, allergy etc. Contrary to the commercial formulations, the instant formulation does not show any side effects as described earlier. The rationale behind the instant formulation encompasses the synergistic activity of the combination of both the active ingredients. The antibacterial and cell proliferation activity of the sericin and sophorolipid enhances cell proliferation and eventually vascularization. Therefore, the instant formulation shows better wound healing capacity.

In an embodiment, the said biodegradable and biocompatible pharmaceutical composition comprises sericin in the range of 8-10% w/w; sophorolipid in the range of 0.01 to 10%; a gelling or thickening agent in the range of 2 to 5%, together with one or more pharmaceutically acceptable carriers/excipients.

In a preferred embodiment, the said gelling or thickening agents may be selected from the group consisting of various gums, Carboxy methylcellulose sodium, sodium alginate, Hydroxypropyl Methylcellulose (HPMC).

In another preferred embodiment, sodium alginate is used as a gelling agent.

In yet another preferred embodiment, the said topical composition may be formulated into variety of formulations selected from the group consisting of cream, ointment, gel, spray or solution using appropriate pharmaceutical carriers/excipients.

In another preferred embodiment, the said composition is formulated as topical gel.

In yet another preferred embodiment, pH of said formulations is maintained at 5.5-6.1.

In yet another embodiment, the invention provides a process for preparation of topical gel comprising the steps:
i) providing cocoons of Bombyx mori;
ii) heat extracting the cocoons as provided in step (i) to form sericin gel;
iii) providing culture of Candida bombicola in 10% glucose solution and 1% vegetable oil to obtain cell broth;
iv) incubating the cell broth as obtained in step (iii) at nearly 28° C., upto 180 rpm for 6-7 days followed by extracting with ethyl acetate to obtain sophorolipid;
v) adding sodium alginate to the sericin gel obtained in step (ii) with continuous stirring;
vi) heating the mixture obtained in step (v) in a water bath at 40-70° C.;
vii) adding sophorolipid obtained in step (iv) to the mixture of step (vi) to form a uniform gel;
viii) sterilizing the uniform gel as obtained in step (vii) under UV light for nearly 20-25 minutes to obtain the wound healing composition.

The formulation thus prepared is further evaluated for its extrudability, swelling index, in-vitro diffusion study, and release kinetics and ex-vivo bio-adhesive strength.

In still yet another embodiment, the present invention provides methods of treating wounds comprises applying to said wound a wound-healing amount of said pharmaceutical composition to the affected area. The period of application will depend on the size and severity of the wound.

In still yet another embodiment, the present invention provides methods of administering said pharmaceutical compositions.

In another preferred embodiment, the said composition is useful for diabetic scar healing and in burns.

In yet another embodiment, the invention provides wound healing testing protocol of the compositions in vitro and in vivo and its efficacy based on the parameters viz., visible observations; wound size measurement; physical examination; drug content determination; viscosity measurement (Rheology); In vitro drug release studies; Drug release kinetic studies; Skin irritation test and Histopathological studies.

In Incision model, the results confirm the faster wound-healing activity of Sericin plus sophorolipids gel. The antioxidant activity is assessed by DPPH scavenging method wherein, the sericin plus sophorolipids gel is found to be most potent antioxidant than the standard gels. Thus the gel composition comprising Sericin plus sophorolipids possesses not only antimicrobial activity but also antioxidant activity and hence provides faster wound healing than the standard gels.

EXAMPLES

The following examples are given by way of illustrations and should not be construed to limit the scope of the present invention.

Example 1

A. Sophorolipid Production

Seed culture was developed by transferring loopful of *Candida bombicola* ATCC 22214 cells from slant, in 10 mL Malt Extract-Glucose-Yeast extract-Peptone (MGYP) medium, followed by incubation at 28° C., 180 rpm for 24 h. This seed culture was transferred to 90 mL of fresh media and incubated for 48 h at 180 rpm, 28° C. After 48 h of growth the culture media was centrifuged at 5000 rpm, for 20 minutes at 10° C. The cell pellet was collected and further subjected to resting cell method.

B. Resting Cell Method

The cell pellet was re-suspended in 10% of glucose solution. 1% oil (Oleic acid) was added to the above solution. For the production of sophorolipids, the cell broth was incubated at 28° C., 180 rpm for 6-7 days with continuous monitoring. This procedure was repeated three times and sophorolipids was extracted for further yield estimation and characterization.

C. Extraction of Sophorolipids

Extraction of sophorolipid was ensued after 7 days when the oil film was visibly vanished from the culture medium. Further the medium was centrifuged at 5000 rpm for 20 minutes at 10° C. to pellet down the cells. Supernatant was collected and extracted with equal volume of ethyl acetate as described in prior art. Anhydrous Sodium sulphate was added to remove any traces of water left. The ethyl acetate was filtered and reduced by rotary evaporation under vacuum to yield a brown colored viscous product that was stored at 4° C.

Example 2: Formulation Details and Process of Preparation

In order to optimize the concentration of gelling agent to achieve proper consistency of the gel, formulations were prepared with different gelling or thickening agents such as various gums, Carboxy methylcellulose sodium, sodium alginate, Hydroxypropyl Methylcellulose (HPMC) with different concentrations of 1 to 8% were tried. The formulations that showed good spreadability and consistency was selected for further studies.

A. Composition of One Preferred Formulation

| Ingredients | Quantity |
| --- | --- |
| Sericin | 8-10% |
| SL(sophorolipid) | 1 mg/ml |
| Sodium alginate | 2-3% |

B. Process for Preparation:

Gelling agent sodium alginate was slowly added to the sericin gel with continuous stirring and heating on water bath (Temp: 40-70° C.). SL (sophorolipid) was added with continuous stirring till a uniform gel was formed. Formed gel was placed under UV light for sterilization upto 20-25 min and stored in plastic container at room temperature.

The prepared gel was inspected visually for their colour and homogeneity. The spreadability (n=3) of the gel formulation was determined by measuring the spreading diameter of 1 g of gel between two horizontal plates (20 cm×20 cm) after one min. The standardized weight tied on the upper plate was 125 g.

The pH was measured at room temperature, in each gel sample using digital pH meter which was calibrated before each use with standard buffer solutions. The pH of the gel formulations was performed at 1, 10, 45 and 60 days after preparation to detect any pH changes with time and the observations on the formulation prepared areas below:

a) Colour: Brown
b) pH determination: 5.5±0.06 to 6.1±0.33
c) Spreadability: 47 to 60±0.50 mm
d) Homogeneity: Homogeneous

Example 3: Wound Healing: Testing Protocol and Results: In Vitro and In Vivo

A. Testing Protocol:

Wister rats (Male) obtained from National Institutional of Bioscience, Pune, Maharashtra weighing 250±20 gm were used and all the studies performed as per CPCSEA guidelines (CPCSEA Reg No. SSBS/AH/04-2015). The animals were housed in a standard individual metal cages and room was maintained at 22±1° C. with an alternating 12 h light-dark cycle. Food and water were provided ad libitum. All the experiments on animals were conducted after obtaining permission from Institutional Animal Ethical Committee of the Institute.

B. Incision Wound Model:

Animals were divided into two groups (six animals each). Body weights of the animals in grams are shown in following table:

TABLE NO. 1

| | GROUPS (wt in grams) | |
| --- | --- | --- |
| ANIMAL | A | B |
| 1 | 270 | 259 |
| 2 | 250 | 266 |
| 3 | 256 | 269 |
| 4 | 245 | 268 |
| 5 | 270 | 240 |
| 6 | 244 | 267 |

All animals of two groups were anesthetized with an aesthetic ether, and a paravertebral long incision of 4.4 cm length were made through the skin and cutaneous muscle at a distance about 1.5 cm from the middle on right side of the depilated back.

All groups (A and B) of animals received sufficient amount of formulation applied externally (as depicted in table No. 2). All the test formulations were applied once a day for 10 days starting from the day of incision. Wound-healing property was evaluated by wound length and wound closure time.

TABLE NO. 2

| GROUP | FORMULATION |
| --- | --- |
| A | Positive control (povidone iodine ointment, commercially available) |
| B | Test group (formulation of sophorolipid with sericin) |
| C | Sericin alone |
| D | Negative control (untreated) |
| E | Sophorolipid alone |

C. Results: Visible Observations

Figure 2:
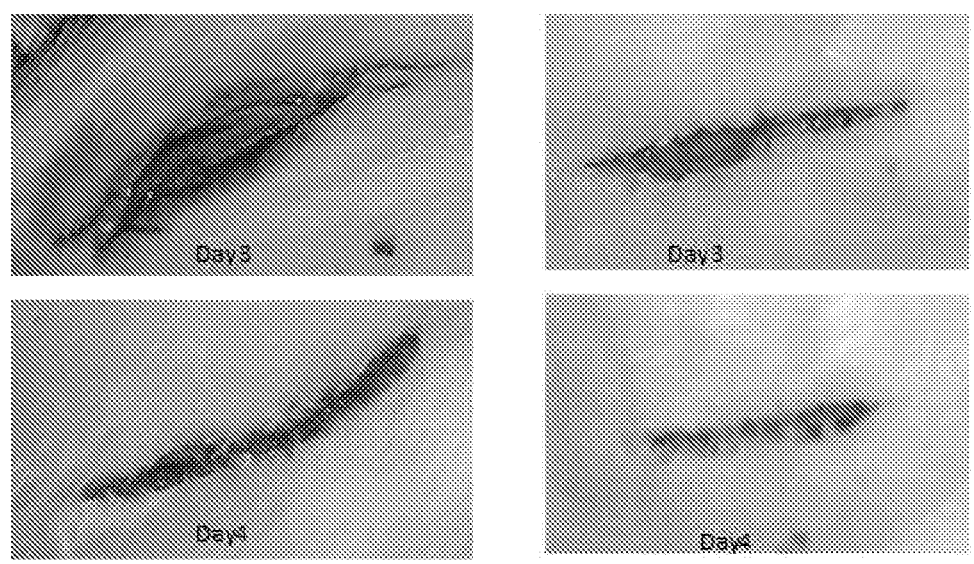
Figure 3:
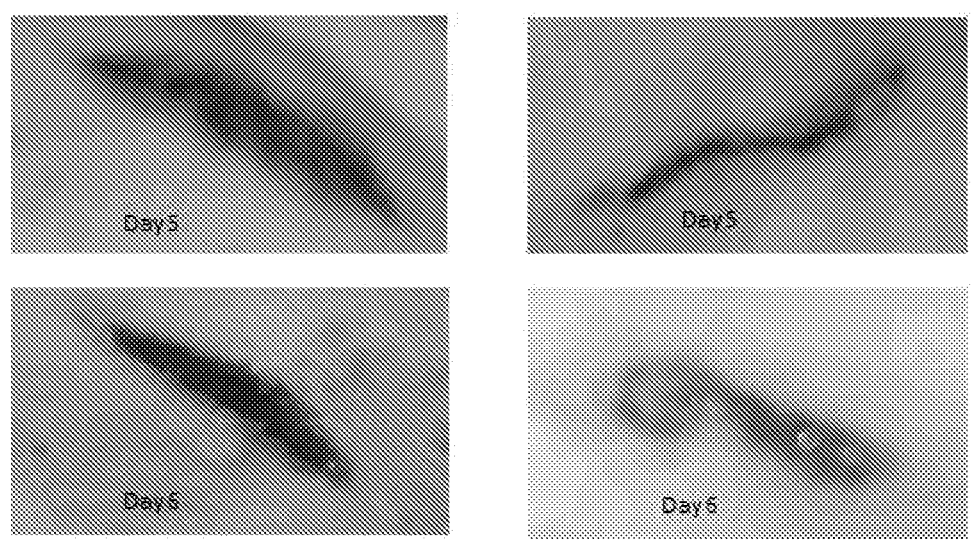
Figure 4:
Figure 5:
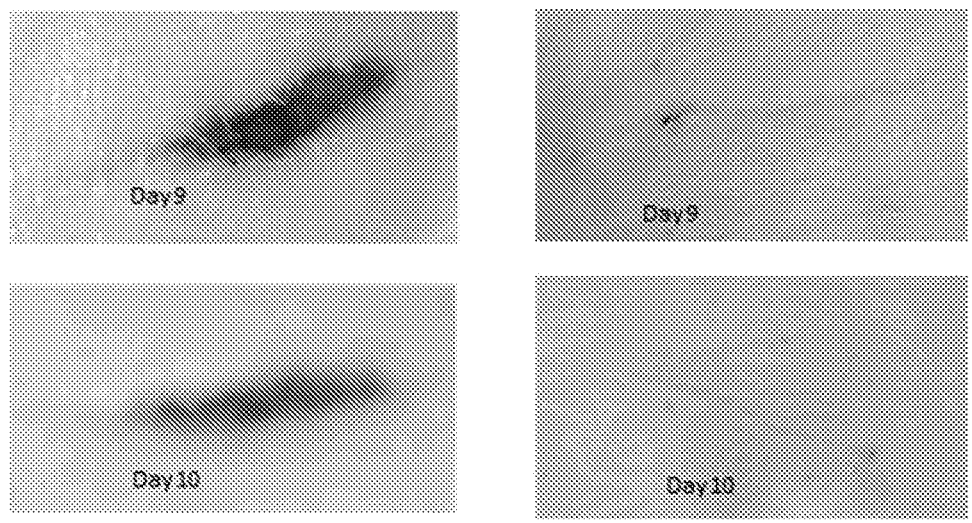

The area of wound was measurement on the days 2, 4, 6, 8, 10 days of post-surgery in all the groups (as shown in FIGS. 1 to 5 respectively). The group, treated with Sericin plus sophorolipids gel, showed fast contraction and healing when compared with control and standard compounds.

There was very rapid closure of the wound treaded with Sericin plus sophorolipids ointment when compared with control and standard compounds. FIGS. 1 to 5 depicts the visible observation of comparative wound healing of the Wister rats (control vis-à-vis group B) by the application of the formulations. The group B treated with the formulation according to the invention not only reduces wound size (in diameter) but also completely diminishes the scar of the wound.

When a wound occurs and is exposed to external environment, it is more prone to attack by microbes, which invade through the skin and delay the natural wound-healing process. Reactive oxygen species (ROS, includes oxygen-derived radicals known as well as non-radical oxidants), often loosely termed "oxidants," are vital part of healing and serve as cellular messengers that drive numerous aspects of molecular and cell biology. ROS can trigger the various beneficial pathways of wound healing, for example, at micro molar concentrations of hydrogen peroxide can promote vascular endothelial growth factor (VEGF) expression in keratinocytes (Khanna et al., 2001). Results obtained in this study confirm the faster wound-healing activity of Sericin plus sophorolipids gel. The antioxidant activity was assessed by DPPH scavenging method wherein, Sericin plus sophorolipids gel was found to be most potent antioxidant than the standard gel. This will confirm that the Sericin+sophorolipids gel not only possesses antimicrobial activity but also possesses antioxidant activity.

Example 4: In Vitro Testing Protocol

1. Wound Size Measurement:

Every alternative days wound size contraction was measured. By placing transparent blotting paper carefully on the wounded part of rats marking were done by permanent marker and size of reduction in wound noted.

TABLE NO. 3

| SR NO | A | B | C | D | E |
|---|---|---|---|---|---|
| DAY 2 | | | | | |
| 1 | 34 | 17 | 24 | 39 | 26 |
| 2 | 27 | 27 | 25 | 40 | 28 |
| 3 | 26 | 27 | 30 | 44 | 25 |
| 4 | 24 | 26 | 30 | 43 | 24 |
| 5 | 35 | 23 | 26 | 43 | 27 |
| 6 | 20 | 24 | 26 | 36 | 26 |
| AVG: | 27.66667 | 24 | 26.83333 | 40.83333 | 26.000 |
| DAY-4 | | | | | |
| 1 | 33 | 9 | 21 | 36 | 25 |
| 2 | 27 | 20 | 23 | 35 | 26 |
| 3 | 25 | 13 | 27 | 38 | 22 |
| 4 | 24 | 18 | 28 | 38 | 21 |
| 5 | 34 | 15 | 24 | 37 | 24 |
| 6 | 20 | 14 | 23 | 31 | 24 |
| AVG: | 27.16667 | 14.83333 | 24.33333 | 35.83333 | 23.666 |
| DAY-6 | | | | | |
| 1 | 31 | 5 | 20 | 34 | 23 |
| 2 | 24 | 10 | 22 | 33 | 24 |
| 3 | 23 | 8 | 25 | 35 | 18 |
| 4 | 22 | 9 | 27 | 34 | 19 |
| 5 | 33 | 9 | 24 | 33 | 21 |
| 6 | 19 | 8 | 22 | 30 | 18 |
| AVG: | 25.33333 | 8.166667 | 23.33333 | 33.16667 | 20.5 |
| DAY-8 | | | | | |
| 1 | 27 | 2 | 18 | 29 | 18 |
| 2 | 22 | 4 | 16 | 28 | 18 |
| 3 | 19 | 6 | 17 | 28 | 15 |

TABLE NO. 3-continued

| SR NO | A | B | C | D | E |
|---|---|---|---|---|---|
| 4 | 20 | 8 | 16 | 30 | 16 |
| 5 | 29 | 3 | 16 | 26 | 17 |
| 6 | 18 | 4 | 15 | 25 | 15 |
| AVG: | 22.5 | 4.5 | 16.33333 | 27.66667 | 16.5 |
| DAY 10 | | | | | |
| 1 | 19 | 1 | 9 | 20 | 10 |
| 2 | 15 | 0 | 6 | 22 | 11 |
| 3 | 15 | 0 | 7 | 23 | 7 |
| 4 | 15 | 0 | 6 | 24 | 7 |
| 5 | 16 | 1 | 6 | 19 | 8 |
| 6 | 9 | 2 | 5 | 18 | 6 |
| AVG: | 14.83333 | 0.666667 | 6.5 | 21 | 8.11 |

From the above, it is evident that the group B treated with the formulation comprising sericin and sophorolipid provides faster and complete wound healing at day 10, from the date of incision, when compared to control/standard/other test formulations.

2. Photographic Comparison

From the above, it is evident that the group B treated with the formulation comprising sericin and sophorolipid provides faster and complete wound healing at day 10 (FIG. 5), from the date of incision, when compared to control and other test formulations.

Example 5: Skin Irritation Test

The skin irritation test was carried out on male Wistar Rats 250±20 gm. The animals were kept under standard laboratory conditions, with temperature of 22° C.±1° C. and relative humidity of 55%±5%. The animals were housed in standard individual metal cages with free access to a standard laboratory diet.

Hair was shaved from back and area of 4 cm$^2$ was marked on both the sides, one side served as control while the other side was test. Gel was applied (500 mg/animal) twice a day for 7 days and the site was observed for any sensitivity and the reaction if any, was graded as 0, 1, 2, 3 for no reaction, slight patchy erythema, slight but confluent or moderate but patchy erythema and severe erythema with or without edema, respectively.

The above test confirms that the formulation according to the invention is safe as it is not provoked any allergic response when applied on the skin.

ADVANTAGES OF INVENTION

Wound healing compositions with naturally derived materials
Free of skin irritation
Economically viable compositions
No side effects

We claim:

1. A pharmaceutical composition for wound healing, comprising:
  a) 8% w/w of silk sericin;
  b) 0.1% of sophorolipid;
  c) 2-5% of a gelling or thickening agent; and
  d) one or more pharmaceutically acceptable ingredients.

2. The pharmaceutical composition as claimed in claim 1, wherein the composition is prepared as a topical formulation; wherein the formulation is selected from the group consisting of an aqueous solution, suspension, dispersion, salve, ointment, gel, cream, lotion, spray or paste.

3. The pharmaceutical composition as claimed in claim 1, wherein the gelling or thickening agent is selected from the group consisting of carboxy methylcellulose sodium, sodium alginate, hydroxypropyl methylcellulose (HPMC).

4. A process for the preparation of a pharmaceutical composition according to claim 1, comprising the steps of:
   i) providing cocoons of *Bombyx mori;*
   ii) heat extracting the cocoons as provided in step (i) to forma sericin gel;
   iii) providing a culture of *Candida bombicola* in 10% glucose solution and 1% vegetable oil to obtain a cell broth;
   iv) incubating the cell broth as obtained in step (iii) at nearly 28° C., up to 180 rpm for 6-7 days followed by extracting with ethyl acetate to obtain sophorolipid;
   v) adding sodium alginate to the sericin gel obtained in step (ii) with continuous stirring;
   vi) heating the mixture obtained in step (v) in a water bath at 40-70° C.;
   vii) adding sophorolipid obtained in step (iv) to the mixture of step (vi) to form a uniform gel; and
   viii) sterilizing the uniform gel as obtained in step (vii) under UV light for nearly 20-25 minutes to obtain the wound healing composition.

5. A method of treating wounds comprising applying a pharmaceutical composition according to claim 1 to a wound area.

6. A method of healing wounds or removing scars comprising applying a pharmaceutical composition according to claim 1 to a wound or scar.

* * * * *